US010466108B2

(12) United States Patent
Brown et al.

(10) Patent No.: US 10,466,108 B2
(45) Date of Patent: Nov. 5, 2019

(54) MOLYBDENUM NITRIDE ABSORBER COATING FOR A DETECTOR

(71) Applicants: Ari D. Brown, Ellicott City, MD (US); Kevin H. Miller, Washington, DC (US); Edward J. Wollack, Clarksville, MD (US)

(72) Inventors: Ari D. Brown, Ellicott City, MD (US); Kevin H. Miller, Washington, DC (US); Edward J. Wollack, Clarksville, MD (US)

(73) Assignee: United States of America as represented by the Administrator of NASA, Washington, DC (US)

( * ) Notice: Subject to any disclaimer, the term of this patent is extended or adjusted under 35 U.S.C. 154(b) by 122 days.

(21) Appl. No.: 15/685,307

(22) Filed: Aug. 24, 2017

(65) Prior Publication Data

US 2019/0063996 A1    Feb. 28, 2019

(51) Int. Cl.
| | |
|---|---|
| *G01J 5/02* | (2006.01) |
| *G01J 5/20* | (2006.01) |
| *H01L 27/146* | (2006.01) |
| *G01N 21/3581* | (2014.01) |
| *G01J 5/08* | (2006.01) |
| *G01N 22/00* | (2006.01) |
| *G01J 5/04* | (2006.01) |

(52) U.S. Cl.
CPC .............. *G01J 5/024* (2013.01); *G01J 5/046* (2013.01); *G01J 5/0853* (2013.01); *G01J 5/20* (2013.01); *G01N 21/3581* (2013.01); *G01N 22/00* (2013.01); *H01L 27/14669* (2013.01)

(58) Field of Classification Search
CPC ....................................................... G01J 5/024
See application file for complete search history.

(56) References Cited

U.S. PATENT DOCUMENTS

| | | | |
|---|---|---|---|
| 9,383,254 B1* | 7/2016 | U-yen ........................ | G01J 1/42 |
| 2006/0214113 A1* | 9/2006 | Kleinerman .............. | G01J 1/58 |
| | | | 250/458.1 |
| 2013/0214160 A1* | 8/2013 | Cazaux ............. | H01L 27/14621 |
| | | | 250/338.4 |
| 2014/0054740 A1* | 2/2014 | Yama ................ | H01L 31/02019 |
| | | | 257/459 |
| 2016/0018267 A1* | 1/2016 | Timofeev ................ | G01J 5/024 |
| | | | 250/336.2 |
| 2016/0181376 A1* | 6/2016 | Utsumi ................. | H01L 21/324 |
| | | | 257/77 |

OTHER PUBLICATIONS

Young et al., "Detector Needs for Long Wavelength Astrophysics", A Report by the Infrared, Submillimeter, and Millimeter Detector Working Group, Jun. 2002, available at https://asd.gsfc.nasa.gov/archive/safer/docs/ISMDWG_final.pdf (Year: 2002).*

* cited by examiner

*Primary Examiner* — Michael C Bryant
*Assistant Examiner* — Jeremy S Valentiner
(74) *Attorney, Agent, or Firm* — Christopher O. Edwards; Bryan A. Geurts (57) ABSTRACT

The present invention relates to an electrically thin molybdenum thin film absorber coating for a detector, that is capable of absorbing a fraction of incident electromagnetic radiation over a 1-15 THz spectral range.

5 Claims, 6 Drawing Sheets

MOLYBDENUM NITRIDE ABSORBER COATING FOR A DETECTOR

ORIGIN OF THE INVENTION

The invention described herein was made by employees of the United States Government, and may be manufactured or used by or for the Government for governmental purposes without the payment of any royalties thereon or therefor.

BACKGROUND OF THE INVENTION

1. Field of the Invention

The present invention relates to an electrically thin, molybdenum thin film absorber coating for a detector, that is capable of absorbing incident electromagnetic radiation over a 1-10 terahertz (THz) spectral range, and, in some instances, over a 1-15 THz spectral range.

2. Description of the Related Art

Impedance matched coatings are used for absorber applications to couple mid-to-far infrared (IR) radiation to a bolometric detector. In very general terms, this means coupling light to a sensor. However, ultrasensitive bolometric detectors typically have constraints on their heat capacity in order to achieve the desired temporal response or detector "time constant". Consequently, these considerations place restrictions on the volume and material properties used to realize an absorber structure.

Historically, the coatings that have been used are difficult to reproduce or are susceptible to aging in atmosphere (ambient). In particular, current approaches of realizing low heat capacity impedance matched absorber coatings include the use of implanted silicon (Si) membranes, non-magnetic disordered alloy thin films (e.g., titanium/gold (Ti/Au), chrome/gold (Cr/Au), palladium/gold (Pd/Au), etc.), semimetals thin films (e.g., bismuth (Bi), and metal foams (e.g., "gold black" and carbon nanotubes)). For thin films the coupling efficiency is typically controlled by the magnitude of the film's surface resistance, the electromagnetic properties and thickness of the supporting substrate material, optional electrical matching layers (i.e., anti-reflection coatings or other circuit networks), and resonant or frequency independent back-terminations, which depend on the end application. For metal foams or other thick film approaches—the coupling efficiency is set by the total coating thickness. Since the absorber will be used cryogenically it is desirable that the residual resistance ratio (RRR) for metal films is of order unity and repeatable upon cooling to the desired operational temperature. This consideration favors the use of disordered conductive materials in defining a thin film absorber structure.

However, present approaches for realizing absorber coatings are generally not acceptable because: (1) as homogenous or alloyed thin film coatings, they are susceptible to aging (Ti/Au, Cr/Au, Pd/Au, Bi), which results in a transient optical efficiency of the sensor; (2) they are high optical efficiency broadband absorbers (i.e., foams like gold black or "meta-materials" such as multi-walled carbon nanotubes), which have relatively high heat capacity, and which impact the speed of the low-background cryogenic detectors and, thus, cannot be used in conjunction with ultrasensitive bolometric detectors at low temperatures; (3) they are reactive in the short wavelength limit (Bi and implanted Si), which correspondingly reduces their optical efficiency; or (4) they add considerable fabrication complexity (e.g., performing an implant on a Si membrane) for some detector architectures.

Further, other coatings for fabrication, which have one or more attributes which do not meet our specifications include: 1) titanium nitride (TiN), which, like Bi, is susceptible to oxidation during oxygen plasma ashing, 2) palladium gold, which has too low a resistivity, and 3) gold (Au), which has a poor adhesion to Si and silicon nitride (SiN), and has too low a resistivity. Moreover, commonly used adhesion promoter materials like molybdenum (Mo) and titanium (Ti) alloy with Au at temperature <100° C., result in either a material with a transient impedance or with an unpredictable residual resistance ratio (RRR).

Accordingly, as more advanced space missions are pursued, the above negative factors can limit applicability of these methods for long duration space missions. Thus, options for new materials for use as low-heat-capacity impedance-matched absorber coatings, that are not reactive in the mid-to-far IR spectral range, are needed.

SUMMARY OF THE INVENTION

The present invention relates to an electrically thin, molybdenum thin film absorber coating for a detector that is capable of absorbing a fraction of incident electromagnetic radiation over a 1-10 THz spectral range, and, in some instances, over a 1-15 THz spectral range.

In one embodiment, the present invention relates to an absorber coating for a detector, including: a molybdenum nitride absorber coating disposed on a substrate; a transition edge sensor disposed on the substrate; wherein an optical surface impedance of the molybdenum nitride absorber coating is one of 377 Ohm/square for a resonant absorber configuration with an electrically thin supporting substrate followed by a reflective back-termination structure (e.g., $R_{sq}$ is equal to the impedance of free-space, $\eta=377$ Ohm/square), or 157 Ohm/square for a frequency independent absorber structure on silicon followed by an absorptive back-termination structure (i.e., $R_{sq}=\eta/(n-1)=157$ Ohm/square, where n=3.4 is the refractive index of the silicon substrate).

However, other coating surface impedance magnitudes can be readily envisioned for other absorber circuit realizations and substrate materials; wherein the molybdenum nitride absorber coating enables absorption of radiation in the 1-15 THz spectral band.

Specifically, in one embodiment, a detector includes: a substrate, on which an absorber coating is disposed; wherein the absorber coating is a molybdenum nitride absorber coating; a transition edge sensor disposed on the substrate; wherein an optical impedance of the absorber coating is predetermined based on a thickness of the absorber coating; wherein the absorber coating enables absorption of electromagnetic radiation in the 1-15 THz spectral range.

In one embodiment, the substrate is a silicon substrate.

In one embodiment, the detector is arranged in a resonant absorber configuration including a reflective back-termination structure; and the thickness of the absorber coating is about 5 nm for a 377 Ohm/square surface impedance.

In one embodiment, an optical efficiency is substantially 100% when used with the reflective back-termination structure spaced a quarter-wave electrical delay from the metalized absorber substrate.

In one embodiment, a thickness of the silicon substrate in the resonant absorber configuration, is about 0.45 micrometers.

In one embodiment, the detector is arranged in a frequency independent configuration including an absorptive back-termination structure; and the thickness of the absorber coating is about 14 nm for a 157 Ohm/square surface impedance.

In one embodiment, an optical efficiency of the absorber coating is substantially 50% when used with the absorptive back-termination structure.

In one embodiment, a thickness of the silicon substrate in the frequency independent configuration, is about 1.45 μm.

In one embodiment, a fabrication process of said molybdenum nitride absorber coating is by deposition via pulsed direct current (DC) reactive magnetron sputtering.

In one embodiment, the molybdenum nitride absorber coating enables absorption of radiation in the 1-10 THz spectral range.

Thus, has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to an electrically thin, molybdenum thin film absorber coating for a detector that is capable of absorbing a fraction of incident electromagnetic radiation over a 1-10 THz spectral range, and, in some instances, over a 1-15 THz spectral range.

In astrophysics instrumentation, the detection bandwidth is a determining factor in the quality of science value and return on investment. One path for realizing far-infrared (IR) instrumentation operating over a wide spectral band (about 1-10 THz) is to employ bolometric sensors with impedance matched absorbers. In particular, an impedance-matched molybdenum nitride ($Mo_2N$) absorber coating was developed which is one important element of bolometric detector assemblies, which defines the sensor's optical efficiency and angular acceptance.

More specifically, in order to overcome the issues of the prior art Bi and Ti/Au absorber coatings, which result in transient optical efficiency, among other negatives and which impact the performance of the low-background cryogenic detectors, and which cannot be used in conjunction with ultrasensitive bolometric detectors, the novel molybdenum nitride ($Mo_2N$) absorber coating of the present invention was developed. The molybdenum nitride absorber coating of the present invention was found to have a stable resistance for very low thickness. Further, the optical impedance of the present coating changed in an asymptotic manner to a steady state value that was 1.07 times greater after 160 days of exposure to at ambient temperature and pressure. Thus, the present $Mo_2N$ absorber coating was easier to reproduce with excellent reliability, at the required spectral range of at least 1-10 THz. Accordingly, the achievable instrumentation lifetime for space missions was increased, and prior functional and fabrication concerns were eliminated.

Note that terms below, such as substantially, approximately, and about, are intended to allow for variances to account for manufacturing tolerances, measurement tolerances, or variations from ideal values that would be accepted by those skilled in the art.

In one embodiment, a resonant absorber design of the present invention for a detector 100 (see FIG. 1), includes the following features: a very thin (~5 nm thickness for a 377 Ohm/square, Tc ~4 K) absorber coating of molybdenum nitride ($Mo_2N$) 101, disposed on a silicon (Si) substrate 102 of 0.45 micrometers, and a Mo/Au transition edge sensor (TES) 103 disposed on the Si substrate 102. With the 377 Ohm/square coating 101, when used in conjunction with a reflective quarter-wave backshort termination 104 ($R_{sq}$ is equal to the impedance of free-space, η=377 Ohm/square), the $Mo_2N$ absorber coating of the present invention achieves 100% efficiency over a resonant band defined by the backshort spacing, and enables absorption of radiation in the 1-10 THz spectral band.

Figure 1:
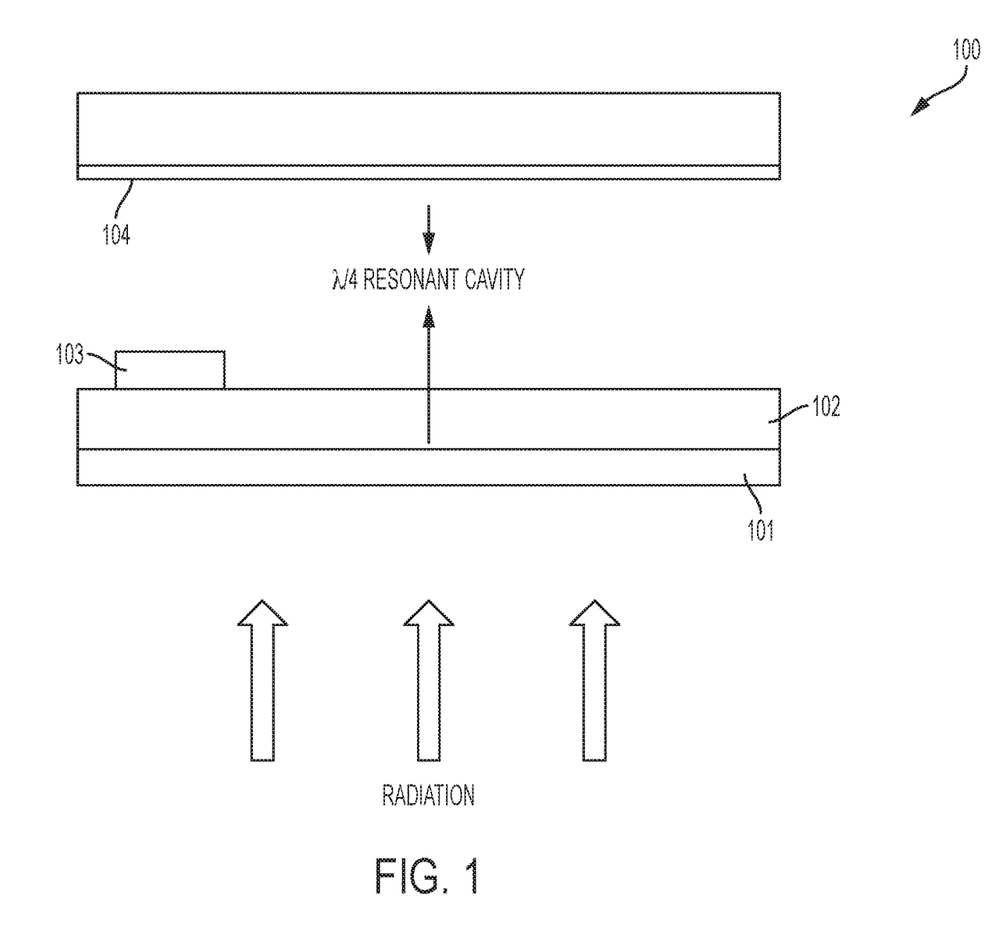
FIG. 1 shows a resonant absorber design of a detector using a molybdenum nitride absorber coating, according to one embodiment consistent with the present invention.

The advantages of using the $Mo_2N$ absorber coating of the present invention are that: 1) it can operate over a controlled spectral band, 2) it has an extremely low heat capacity, and 3) it is thermally and chemically stable in ambient conditions. Thus, the $Mo_2N$ absorber coating of the present invention is a material which can be used in bolometric sensors due to its low heat capacity. With a higher heat capacity, there is a lower sensitivity, so to achieve the desired higher sensitivity, a material with a lower heat capacity must be used. Other coatings, such as have been used in the prior art, are susceptible to aging which degrades their absorption efficiency over time.

The molybdenum nitride (Mo$_2$N) absorber coating of the present invention includes the following novel and positive features, which contrasts to prior art coatings: 1) it is not reactive in the mid-to-far IR spectral range (0.1-15 THz); 2) it has a resistivity greater than 100 μΩ cm (i.e., thus the coating's thickness is greater for higher impedance films relative to other homogenous materials); 3) it has an demonstrated impedance range of: 50-377 Ω/square at 20° Kelvin; 4) it is able to be deposited inside a high vacuum chamber; 5) its coating impedance has been demonstrated not to change more than 5% upon annealing at 150° C. in atmosphere for 1 hour, or more than 10% upon oxygen plasma ashing at 100 W for 20 min in 100 mT of oxygen; 6) its residual resistance ratio (RRR), which is defined as its sheet resistance at 300 K divided by its sheet resistance at 10 K, is 0.9.

The present invention has produced surface resistance values in the range 50<η<377 ohms/square by the methods disclosed below. The physics and underlying circuit employed for the absorber structures drives the desired materials parameters—however, other realizations may desire other coating and materials properties. As long as the film's physical thickness is small compared to the field penetration (or electrical skin) depth, δ, at the free-space wavelength, λ, of interest, the reactance of the film will negligible and the coating will present the desired properties for the transmission line circuit. The for a normal metal field penetration depth can be computed from $\delta = (2/\mu\sigma\omega)^{0.5}$, where μ and σ are, respectively, the electromagnetic permeability and electrical conductivity for the coating, and is $\omega = 2\pi/\lambda$ the observing frequency of the incident radiation in the optical band of interest. Physically, the thin film will approximate an ideal resistor in this limit.

The above physical consideration sets the upper frequency scale the coating can be used. (note that this condition is not realized for bismuth films at high frequencies). If the coating is used at temperature below its superconducting transition temperature—the material be superconducting and will not serve as an ideal resistor for the absorber structure. This consideration sets the lowest frequency the material can be used to approximate a thin film resistor. Thus, the maximum and minimum frequency the coating will approximate its desired absorptive properties is a function of the thickness over the skin depth and the operating temperature.

However, with respect to the above, where film thickness compared to field penetration depth leads into material properties above and below the gap, in ultra-thin films the disorder can dominate and superconductivity will not be realized, since this limit is not universally quantifiable across superconducting materials. For coatings produced and characterized this was not a limiting consideration.

In another embodiment, a frequency independent design of the present invention for a detector 200 (see FIG. 2), includes a ~157 Ohm/square absorber coating 201, about 14 nm in thickness (Tc ~5.1° K), disposed on a 1.45 μm Si substrate 202 (i.e., $R_{sq} = \eta/(1-n)$, where n is the refractive index of the substrate), with a Mo/Au TES 203 disposed on the Si substrate 202. An absorptive back-termination (204) is employed to control stray radiation. The resonant design utilizes a different optical impedance (Ohm/square) than the frequency independent absorber design (i.e., 157 Ohm/square vs. 377 Ohm/square).

Figure 2:
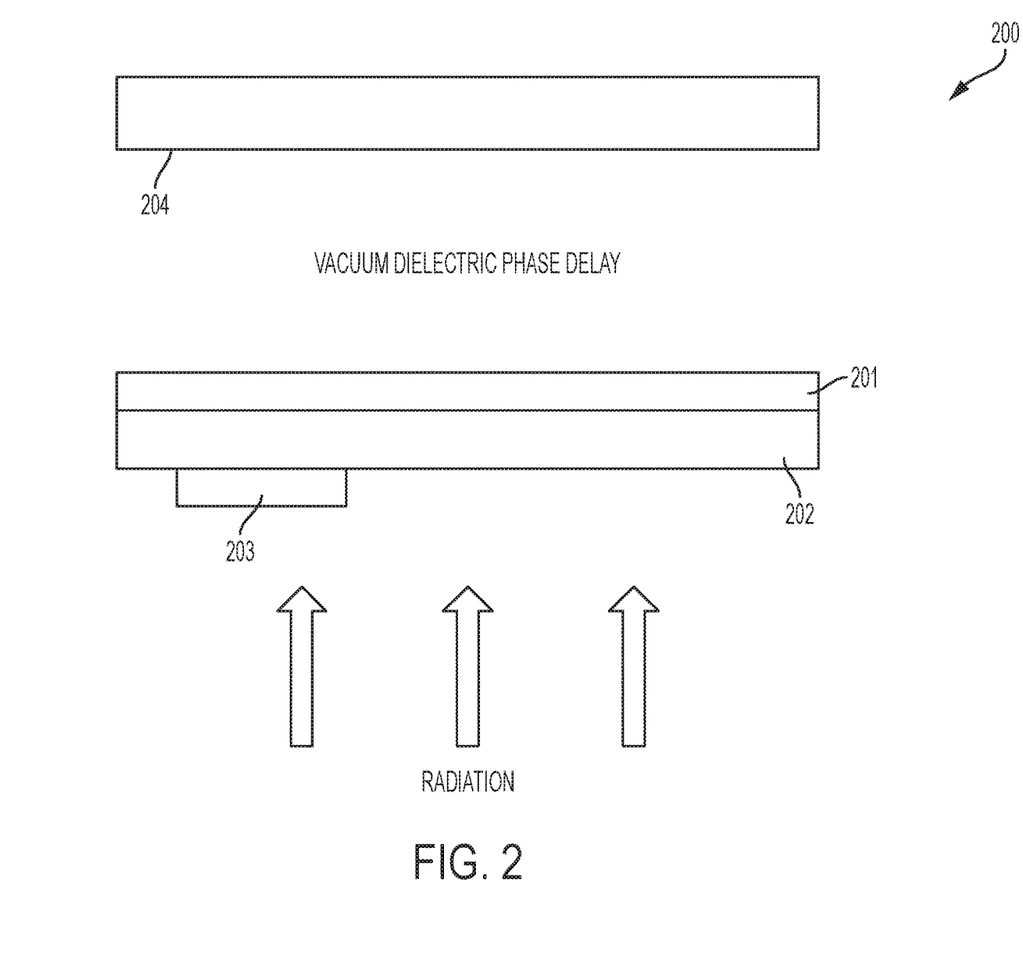
FIG. 2 shows a frequency independent design of a detector using a molybdenum nitride absorber coating, according to another embodiment consistent with the present invention.

With the frequency independent design, the 157 Ohm/square optical impedance with an absorptive back-termination provides a broadband absorption response and the optical efficiency is 50%, as compared to the 100% of the resonant design employing a reflective termination at a quarter wave delay. However, the present invention provides a choice of narrowband or broadband, using a different optical impedance for the absorber coating. Thus, if broadband is desired, the frequency independent design can be used, with the knowledge that the lower optical efficiency is acceptable.

Figure 3:
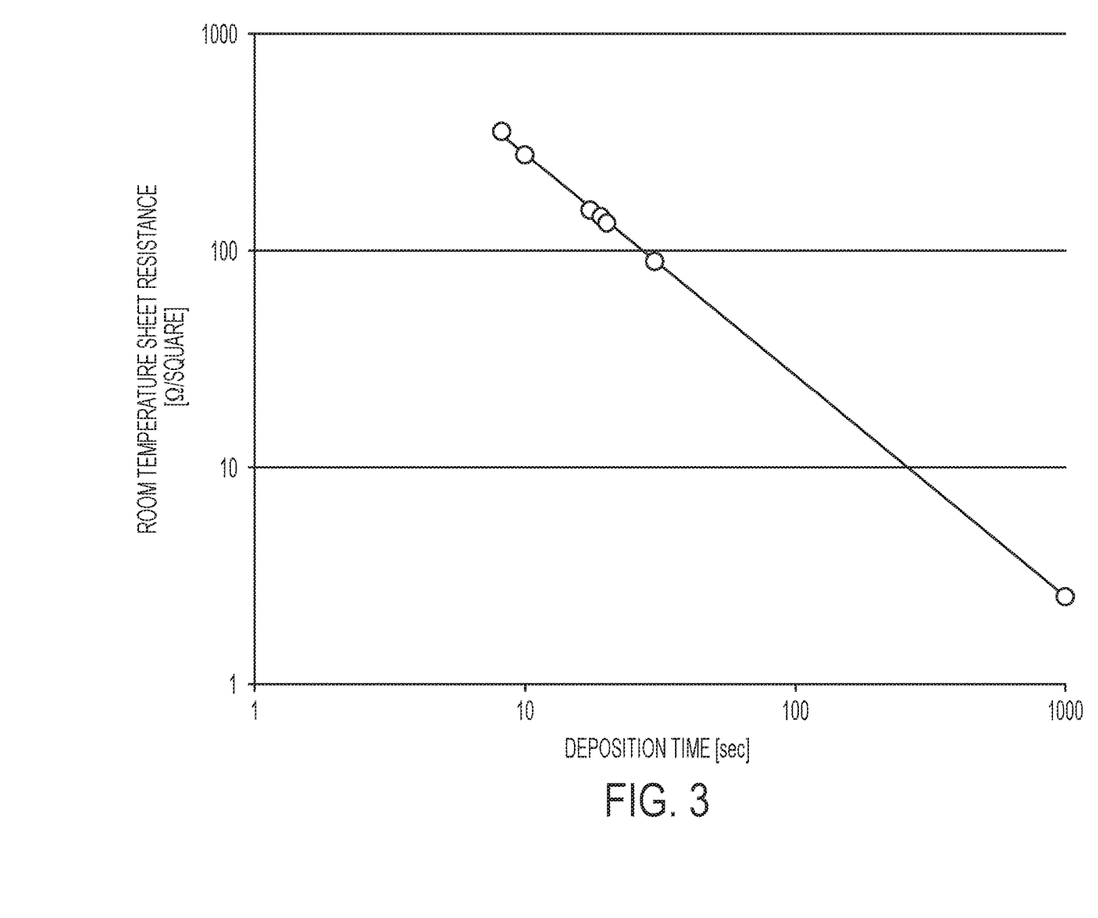
FIG. 3 shows a sheet resistance vs. deposition time graph, according to one embodiment consistent with the present invention.

Thus, the utility of the molybdenum nitride (Mo$_2$N) coating is dictated by its optical impedance, which approximates as its sheet resistance, and a power law relationship between deposition time and sheet resistance shows that deposition time (in seconds) decreases dramatically with a drop in room temperature sheet resistance (Ohm/square) (see FIG. 3). Therefore, by using a power law fit, one can estimate the deposition time required to obtain the desired sheet resistance. Thus, to obtain the thickness of the coating, using 7.6 Angstroms/sec as the deposition rate, and with the deposition time being directly proportional to the thickness, the deposition time is multiplied by the deposition rate value, to obtain the coating thickness.

Other embodiments can be readily envisioned for other substrate materials and can be readily made by suitably changing the metal/dielectric thickness for both the resonant and frequency independent configurations defined.

The fabrication process of the innovation involves deposition of the Mo$_2$N absorber coating onto a bolometric detector pixel. Prior to deposition on the detector pixel, a deposition of the Mo$_2$N coating is conducted on an approximate Si witness. Fabrication of the absorbing thin film of the present invention involves deposition of the molybdenum nitride (Mo$_2$N) via pulsed direct current (DC) reactive magnetron sputtering. The methodology used to deposit the thin film is generally consistent with existing DC reactive magnetron sputtering methods.

Figure 4:
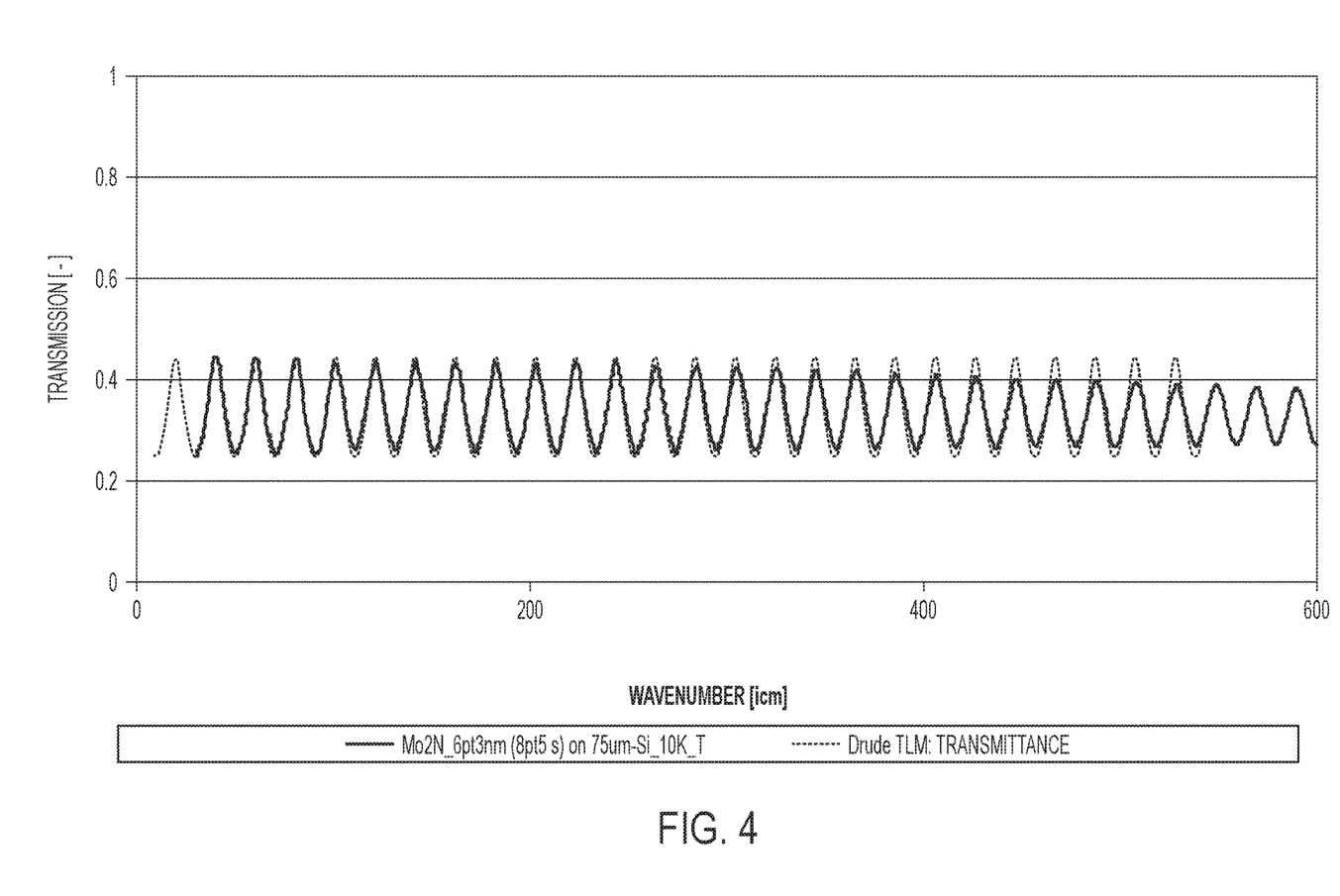
FIG. 4 shows the measured and modeled transmission spectrum for an optical impedance of the 377 Ohm/square coating on a silicon substrate at 10 K, according to one embodiment consistent with the present invention.

For test data and analysis of capabilities at 10° K, transmissivity measurements through a representative sampling of Mo$_2$N-coated Si witness samples are shown in FIG. 4, which shows the optical impedance of the 377 Ohm/square coating, used in the resonant absorber configuration at 10° K.

Figure 5:
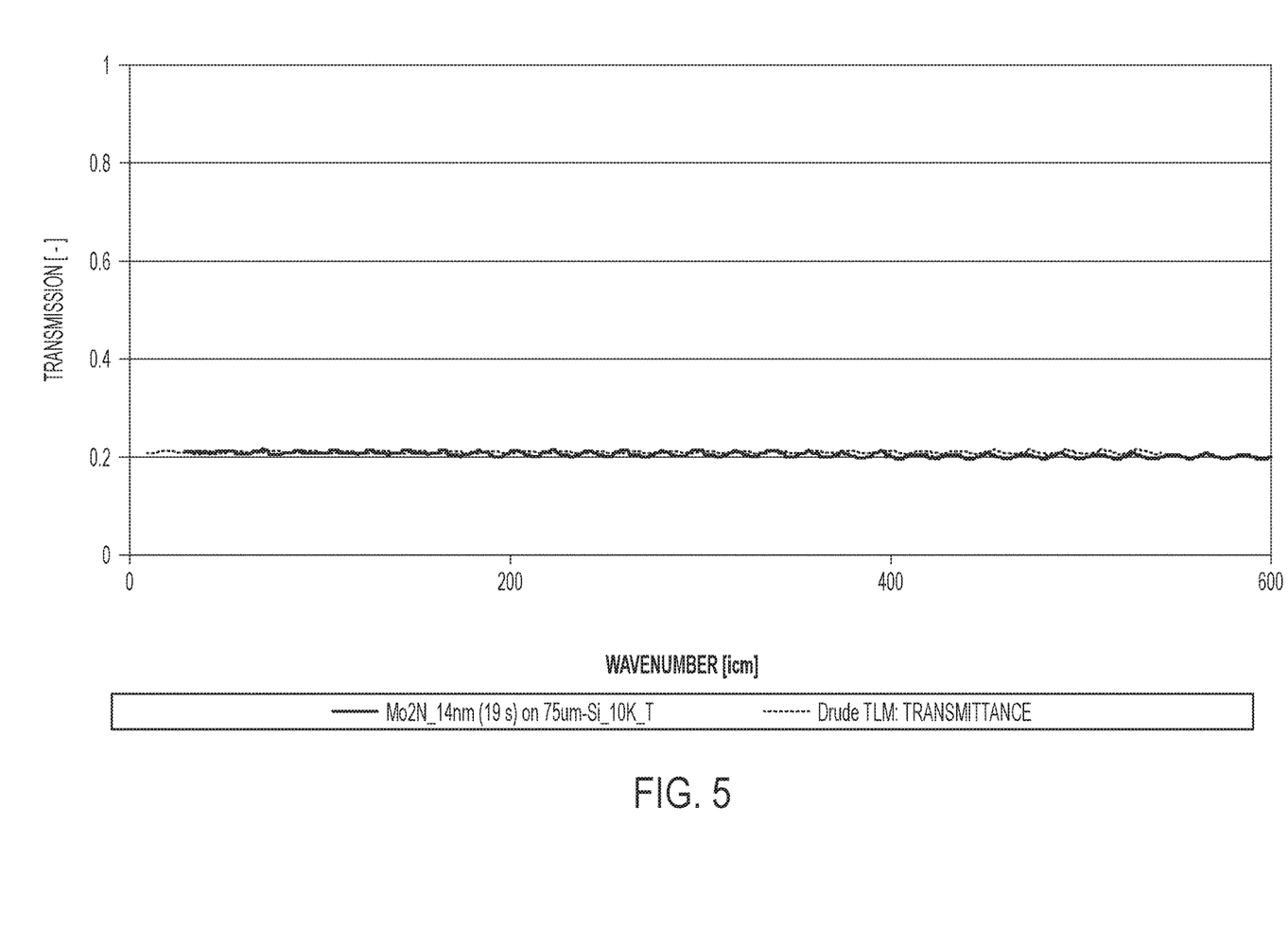
FIG. 5 shows the measured and modeled transmission spectrum for an optical impedance of the 157 Ohm/square coating on a silicon substrate at 10° K, according to one embodiment consistent with the present invention.

Further, FIG. 5 shows the transmissivity measurements through Mo$_2$N-coated Si samples, with an optical impedance of 157 Ohm/square, in the frequency independent arrangement at 10° K.

Figure 6:
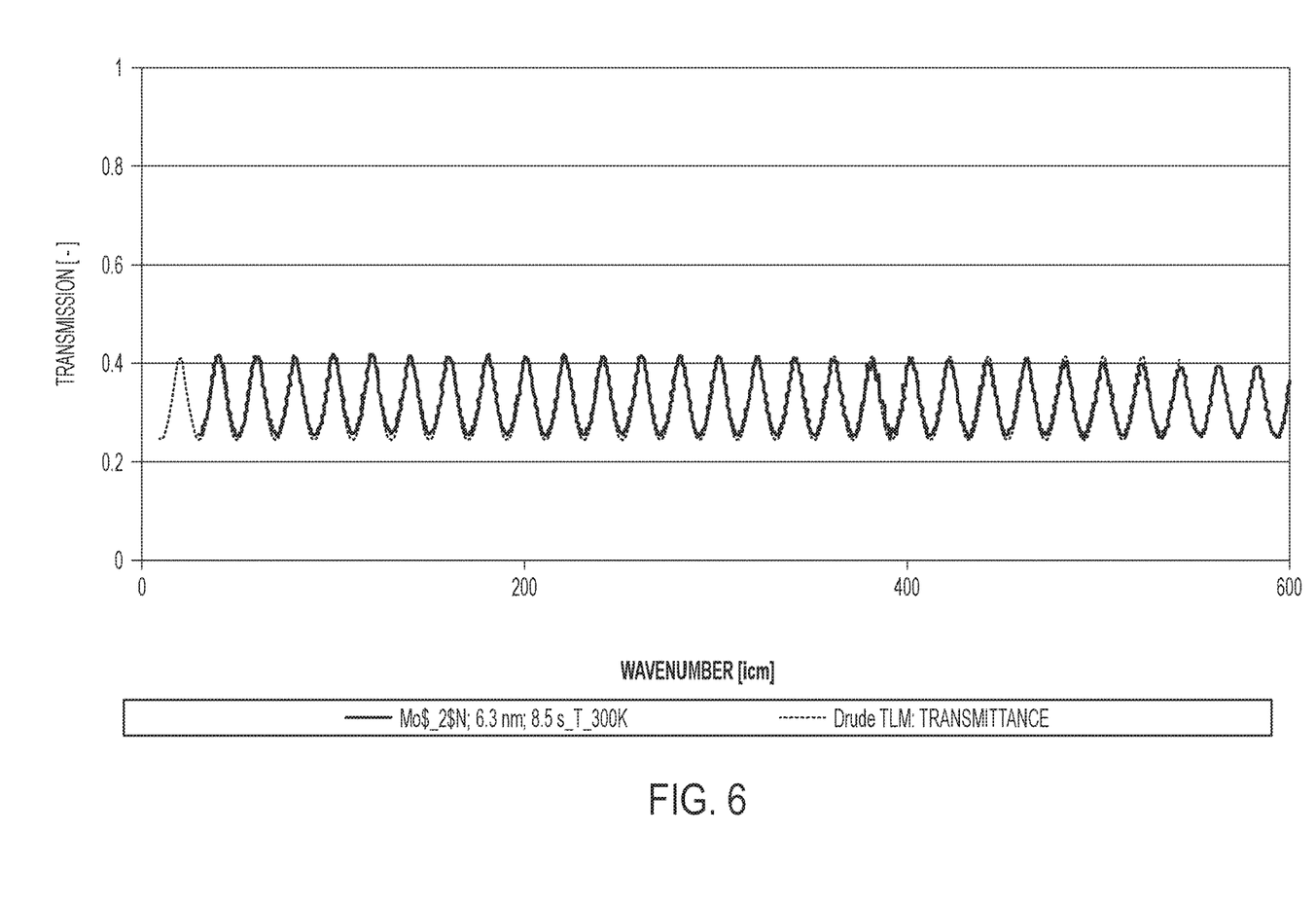
FIG. 6 shows the measured and modeled transmission spectrum for an optical impedance of the 340 Ohm/square coating on a silicon substrate at 300° K, according to one embodiment consistent with the present invention.

Finally, for test data and analysis of capabilities at room temperature, FIG. 6 shows the transmissivity measurements through Mo$_2$N-coated Si samples, with an optical impedance of 340 Ohm/square at 300° K.

The test data shows that all the absorber coatings are well-approximated by a resistive coating over a 1-10 THz spectral range (33-333 icm) and some are resistive to 15 THz.

The present invention is used for the development of THz imagers, and will be advantageous in more advanced, long duration space missions.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A detector, comprising:
a silicon substrate, on which an absorber coating is disposed;
wherein said absorber coating is a molybdenum nitride absorber coating;
a transition edge sensor disposed on said substrate;
wherein an optical impedance of said absorber coating is predetermined based on a thickness of said absorber coating;
wherein said absorber coating enables absorption of electromagnetic radiation in the 1-15 terahertz (THz) spectral range;
wherein said absorber coating is configured to absorb the electromagnetic radiation, the transition edge sensor is configured to receive the absorbed radiation from and passed through said absorber coating; further
wherein the detector is arranged in a frequency independent configuration including an absorptive back-termination structure; and
wherein said thickness of said absorber coating is about 14 nanometers (nm) for a 157 Ohm/square surface impedance.

2. The detector of claim 1, wherein an optical efficiency is substantially 100% when used with said reflective back-termination structure.

3. The detector of claim 1, wherein a thickness of said silicon substrate is about 0.45 micrometers.

4. The detector of claim 3, wherein a thickness of said silicon substrate is about 1.45 micrometers.

5. The detector of claim 1, wherein said molybdenum nitride absorber coating enables absorption of radiation in the 1-10 THz spectral range.

* * * * *